United States Patent [19]

Sisti et al.

[11] Patent Number: 5,688,977
[45] Date of Patent: Nov. 18, 1997

[54] METHOD FOR DOCETAXEL SYNTHESIS

[75] Inventors: Nicholas J. Sisti, Jeffersonville; Charles S. Swindell, Merion, both of Pa.

[73] Assignees: NaPro BioTherapeutics, Inc., Boulder, Colo.; Bryn Mawr College, Bryn Mawr, Pa.

[21] Appl. No.: 616,467

[22] Filed: Mar. 19, 1996

Related U.S. Application Data

[63] Continuation-in-part of Ser. No. 609,083, Feb. 29, 1996.
[51] Int. Cl.$^6$ .................................................. C07D 305/14
[52] U.S. Cl. .................................................. 549/510
[58] Field of Search ................................. 549/510

[56] References Cited

U.S. PATENT DOCUMENTS

| | | | |
|---|---|---|---|
| Re. 34,277 | 6/1993 | Denis et al. | 549/510 |
| 4,814,470 | 3/1989 | Colin et al. | 549/510 |
| 4,857,653 | 8/1989 | Colin et al. | 549/510 |
| 4,924,011 | 5/1990 | Denis et al. | 549/510 |
| 4,924,012 | 5/1990 | Colin et al. | 549/510 |
| 4,960,790 | 10/1990 | Stella et al. | 549/510 |
| 5,015,744 | 5/1991 | Holton | 549/510 |
| 5,136,060 | 8/1992 | Holton | 549/510 |
| 5,399,726 | 3/1995 | Holton et al. | 549/510 |
| 5,422,364 | 6/1995 | Nicolaou et al. | 549/510 |
| 5,466,834 | 11/1995 | Holton et al. | 549/510 |
| 5,475,011 | 12/1995 | Ojima et al. | 549/510 |
| 5,530,020 | 6/1996 | Gunawardana et al. | 549/510 |

FOREIGN PATENT DOCUMENTS

| | | |
|---|---|---|
| 0400971 | 5/1990 | European Pat. Off. |
| 0528729A1 | 8/1992 | European Pat. Off. |
| 2687150 | 2/1992 | France |
| WO91/13066 | 9/1991 | WIPO |

OTHER PUBLICATIONS

"Application of the Vicinal Oxyamination Reaction With Asymmetric Induction to the Hemisynthesis of Taxol and Analogues", L. Mangatal et al, *Tetrahedron*, vol. 45, No. 13, pp. 4177 to 4190, 1989.

"Synthesis of Biologically Active Taxol Analogues with Modified Phenylisoserine Side Chains", Goerg et al., *J. Med. Chem.*, 1992, 35, 4230–4237.

"Biologically Active Taxol Analogues with Deleted A–Ring Side Chain Substituents and Variable C–2' Configurations", Swindell et al, *Journal of Medicinal Chemistry*, 1991, vol. 34, No. 3, pp. 1176–1184.

"New and Efficient Approaches to the Semisynthesis of Taxol and its C–13 Side Chain Analogs by Means of B–Lactam Synthon Method", Ojima et al, *Tetrahedron*, vol. 48, No. 34, pp. 6985–7012, 1992.

"Improved Protection and Esterification of a Precursor of the Taxotere and Taxol Side Chains," Commercon et al, *Tetrahedron*, vol. 33, No. 36, pp. 5185–5188, 1992.

"Highly Sterocontrolled and Efficient Preparation of the Protected, Esterification–Ready Docetaxel (Taxotere) Side Chain", Kanazawa et al, *J. Org. Chem*, vol. 59, No. 6, pp. 1238–1240, 1994.

"Novel Biologically Active Taxol Analogues:Baccatin III 13–(N–(p–Chlorobenzoyl)–(2'R,3'S)–3'–phenylisoserinate) and Baccatin III 13–(N–Benzoyl–(2'R, 3'S)–3'–(p–chlorophenyl)isoserinate)," Georg et al, *Bioorganic & Medicinal Chem. Letters*, vol. 2, No. 4, pp. 295–298, 1992.

*Primary Examiner*—James H. Reamer
*Attorney, Agent, or Firm*—Timothy J. Martin; Michael R. Henson

[57] ABSTRACT

A method of producing docetaxel comprises the esterification of C7, C10 di-CBZ 10-deacetyl baccatin III and an N-CBZ C2'-protected 3-phenyl isoserine side chain wherein C2' is protected by a hydrogenatable benyl-type protecting group. The C7, C10 carbobenzyloxy groups are then replaced with hydrogen and the carbobenzyloxy group at the C3' nitrogen site is replaced with t-butoxycarbonyl. Finally, the resulting compound is deprotected at C2' by replacing the benzyl-type protecting group with hydrogen to produce docetaxel. The esterification preferably employs an excess, such as six equivalents, of the side chain for each equivalent of the C7, C10 di-CBZ 10-deacetyl baccatin III. Benzyloxymethyl is the preferred protecting group at C2'.

24 Claims, No Drawings

METHOD FOR DOCETAXEL SYNTHESIS

RELATED APPLICATION

This application is a continuation-in-part of our earlier application, Ser. No. 08/609,083, filed Feb. 29, 1996 and entitled, Intermediate For Docitaxel Synthesis and Production Method Therefor.

FIELD OF THE INVENTION

This invention generally relates to the synthesis of docetaxel from precursor compounds. More particularly, though, this invention concerns the synthesis of docetaxel using a suitably protected 10-deacetyl baccatin III backbone which is esterified with a suitably protected side chain acid to produce an intermediate that may thereafter be deprotected, acylated and further deprotected to produce docetaxel.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity.

Paclitaxel is a naturally occurring taxane diterpenoid which is found in several species of the yew (genus Taxus, family Taxaceae). Unfortunately, the concentration of this compound is very low. The species of evergreen are also slow growing. Even though the bark of the yew trees typically exhibits the highest concentration of paclitaxel, the production of one kilogram of paclitaxel requires approximately 16,000 pounds of bark. Thus, the long term prospects for the availability of paclitaxel through isolation are discouraging.

While the presence of paclitaxel in the yew tree is in extremely low concentrations, there are a variety of other taxane compounds, such as baccatin III, cephalomannine, 10-deacetylbaccatin III, etc., which are also able to be extracted from the yew bark. Some of these other taxane compounds are more readily extracted in higher yields. Indeed, a relatively high concentration of 10-deacetylbaccatin III can be extracted from the leaves of the yew as a renewable resource.

Among the various taxane compounds which have been found to exhibit anti-tumor activity is the compound known as "docetaxel". This compound is also sold under the trademark TAXOTERE® by Rhone-Poulenc Sante. Docetaxel has the formula as follows:

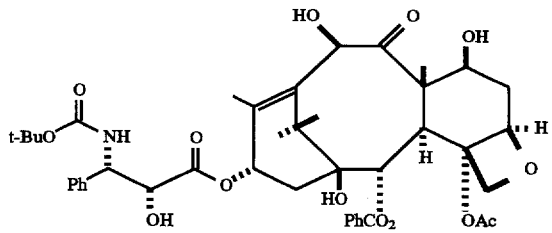

As may be seen in this formulation, docetaxel is similar to paclitaxel except for the inclusion of the t-butoxycarbonyl (t-BOC) group at the C3' nitrogen position of the isoserine side chain and a free hydroxy group at the C10 position. Several possible syntheses of docetaxel and related compounds have been reported in the Journal of Organic Chemistry: 1986, 51, 46; 1990, 55, 1957; 1991, 56, 1681; 1991, 56, 6939; 1992, 57 4320; 1992, 57 6387; and 1993, 58, 255.

In order to successfully synthesize docetaxel, convenient access to a chiral, non-racemic side chain and an abundant natural source of a usable baccatin III backbone as well as an effective means of joining the two are necessary. However, the esterification of the side chain to the baccatin III backbone is difficult because of the hindered C13 hydroxyl in the baccatin III backbone which is located within the concave region of the hemispherical taxane skeleton. This difficulty of synthesis is present both for the synthesis of docetaxel as well as for the synthesis of paclitaxel.

One technique for the semi-synthesis of paclitaxel is found in co-pending patent application Ser. No. 08/483,081. In this application, paclitaxel is synthesized from C7 TES protected baccatin III with N-carbamate protected C2' hydroxyl-benzyl protected (2R,3S)-3-phenyl isosserine A-ring side chain with a hydrogenable benzyl-type protecting group, such as a benzyloxymethyl (BOM) protecting group at the C2' location for the side chain. Following the condensation of the C7 TES protected baccatin III and the side chain, the compound may be suitably deprotected, acylated, and further deprotected to yield paclitaxel.

While, the existing techniques for synthesizing docetaxel certainly have merit, there is still a need for improved chemical processes which can produce this anti-cancer compound. The present invention is directed to such a procedure utilizing the N-carbamate protected C2' hydroxyl benzyl protected (2R,3S)-3-phenylisoserine A-ring side chain as described in my earlier co-pending application.

SUMMARY OF THE INVENTION

It is an object of the present invention to provide a new, useful and efficient protocol for the attachment of a protected A-ring side chain to a protected baccatin III skeleton which may then be converted into docetaxel.

It is still a further object of the present invention to provide a new and useful protocol for the semi-synthesis of docetaxel in an effort to produce a high yield of docetaxel in a cost efficient manner.

Yet another object of the present invention is to provide a method for the production of docetaxel which potentially can be scaled to commercial implementation.

According to the present invention, then, a new and useful method for producing docetaxel is provided. According to the general method, C7, C10 di-CBZ 10-deacetyl baccatin III of the formula:

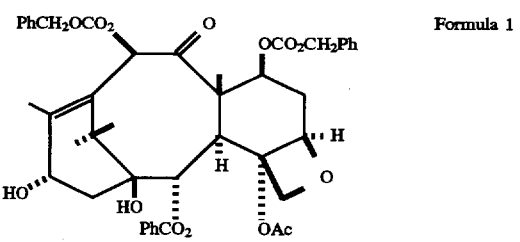

Formula 1 is esterified with an N—CBZ C2'-protected 3-phenylisoserine side chain of the formula:

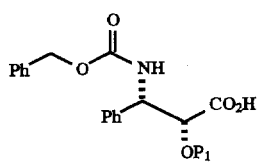

to form a first intermediate compound of the formula:

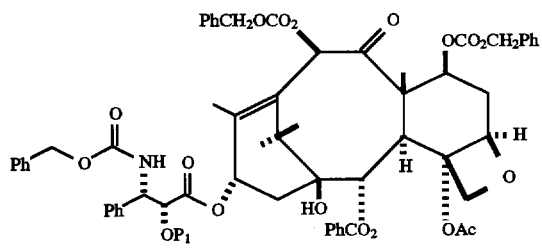

wherein $P_1$ is a hydrogenable benzyl-type protecting group. Next, the C7, C10 carbobenzyloxy in the first intermediate compound is replaced with hydrogen and the carbobenzyloxy at the C3' nitrogen site is replaced with t-BOC to form a second intermediate compound of the formula:

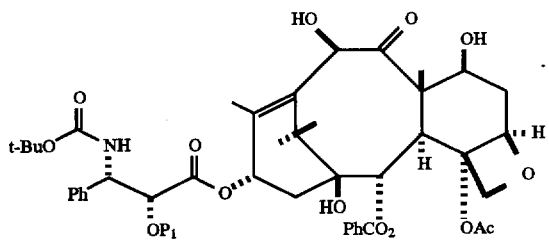

wherein $P_1$ is a hydrogenatable benzyl-type protecting group. Thereafter, the second intermediate compound is deprotected by replacing $P_1$ with hydrogen thereby to produce docetaxel. It is preferred that the hydrogenatable benzyl protecting group be selected from a group consisting of benzyloxymethyl and benzyl with benzyloxymethyl being the preferred protecting group.

During esterification, it is preferred that an excess N—CBZ C2'-protected 3-phenylisoserine be employed, and it is desirable that six equivalents of this side chain be used for each equivalent of a C7, C10 di-CBZ 10-deacetyl baccatin III during esterification. This reaction is preferably performed by dissolving the two compounds in toluene to form a first solution after which dimethylamine pyridine (DMAP) and a dialkylcarbodiimide is added to the first solution. The dialkylcarbodiimide is preferably in equal proportion to the amount of the side chain compound. This dialkylcarboiimide is selected from a group consisting of a diisopropylcarbondiimide and dicyclohexylcarbondiimide. This esterification step is conducted at a first temperature of about 60° to 80° C. for a first interval of time, approximately one to five hours after which the solution is allowed to cool to room temperature. Next, an equal volume of diethyl ether is added, and the resulting solution is cooled to a reduced second temperature of 0° C. or less for a second interval of about twenty-four hours.

Moreover, it is preferred to dissolve the first intermediate compound in a solution and elute this solution to purify the first intermediate compound before deprotecting at C7 and C10 and at the C3' nitrogen site. Here, also, the step of replacing the C7 and C10 carbobenzyloxy groups with hydrogen is conducted first to produce an amine after which the carbobenzyloxy group at the C3' nitrogen site is subsequently replaced with t-BOC to produce the second intermediate compound. The first portion of this reaction is accomplished by dissolving the first intermediate compound in isopropanol/ethyl acetate in the presence of Pearlman's catalyst to form a first mixture and then hydrogenating the first mixture for at least forty-eight hours. The next step in the replacement is accomplished by taking the amine up in tetrahydrofuran and then adding a tertiary amine base. The addition of the tertiary amine base is followed by the addition of di-tert-butyl dicarbonate in order to form C2'-$OP_1$ docetaxel. This second mixture is stirred for about twenty-four hours and reduced in vacuum. It is next redissolved in ethyl acetate, and washed with water and brine. This produces an organic phase which may be separated and chromotagraphed with ethyl acetate:hexane and/or recrystallized to give the second intermediate compound in purified form.

The step of deprotecting the second intermediate compound is then accomplished by dissolving the second intermediate compound in isopropanol and ethyl acetate in the presence of Pearlman's catalyst to form a second mixture. The second mixture is then hydrogenated for at least twenty-four hours.

These and other objects of the present invention will become more readily appreciated and understood from a consideration of the following detailed description of the exemplary embodiments.

DETAILED DESCRIPTION OF THE EXEMPLARY EMBODIMENTS

The present disclosure is broadly directed to a chemical process for the efficient production of docetaxel as well as intermediates and precursors therefor. More specifically, the present invention discloses a new chemical compound in the form of C7, C10-di-CBZ 10-deacetylbaccatin III as a useful intermediate in the production of docetaxel. The C7, C10-di-CBZ 10-deacetylbaccatin III is esterified with a 3-phenylisoserine acid having a hydrogenable benzyl-type protecting group at C2' to the C13 hydroxyl of the baccatin III backbone. The general process described herein involves the production of the C7, C10-di-CBZ 10-deacetylbaccatin III backbone, the production of the suitably protected 3-phenylisoserine acid having the hydrogenatable benzyl protecting group C2', the condensation of the two compounds, and the subsequent deprotection, acylation at the C3' nitrogen site to add the t-butoxycarbonyl group, followed by further deprotection to yield docetaxel.

A. Production of C7, C10 dicarbobenzyloxy 10-deacetylbaccatin III

C7, C10 di-CBZ 10-deacetylbaccatin III (Formula 1) is produced by the following reaction:

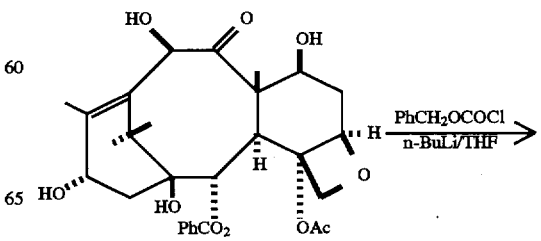

-continued
Reaction I

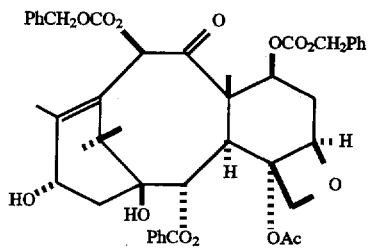

Reaction I

Here, 10-deacetylbaccatin III is dissolved in anhydrous THF (tetrahydrofuran) and is cooled under a nitrogen atmosphere to a temperature of less than −20° C. but preferably −78° C. n-butyl lithium (1.6M in hexane) is added dropwise and the solution is stirred at the reduced temperature for approximately five minutes. At least 1.5 equivalents of n-butyl lithium are needed to get significant product yield, however 2 equivalents are preferable. Benzyl chloroformate is then added dropwise (again, at least 1.5 equivalents of the benzyl chloroformate are needed for significant yield, but 2 equivalents are preferred) and the mixture is stirred over a period of one hour during which time it is allowed to warm to a temperature of no more than 0° C. The mixture is then quenched with cold saturated ammonium chloride to eliminate any excess n-butyl lithium and acetyl chloride, and the mixture is reduced under vacuum. The residue is taken up in ethyl acetate and washed once with water and then with brine to remove unwanted salts. The organic layer may then be dried and reduced under vacuum, and the residue recrystallized or column chromotagraphed with ethyl acetate/hexane to yield C7, C10 di-CBZ 10-deacetylbaccatin III as a white solid in greater than 80% overall yield.

B. Production of the 3-Phenylisoserine Side Chain

The production of the (2R,3S) N—CBZ C2' O-protected 3-phenylisoserine ethyl ester side chain, where the C2' hydroxy group is protected by a hydrogenatable benzyl-type protecting group (Formula 2) can be accomplished from the starting compound (2R, 3S) 3-phenylisoserine ethyl ester according to the following two reactions. The first reaction is:

Reaction II

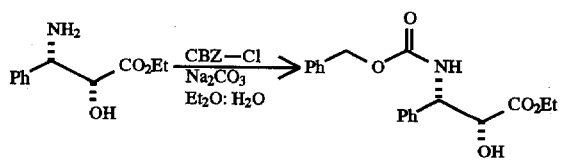

Reaction II

Here, (2R, 3S) 3-phenylisoserine ethyl ester was alternatively dissolved in either equal parts diethyl ether:water or equal parts methyl t-butyl ether:water and the solution was cooled to 0° C. The sodium carbonate was then added to the solution and benzylchloroformate was added dropwise over an interval of about five minutes and the resulting mixture stirred at 0° C. for approximately one hour. After the one hour stirring, the solution was then poured into water and extracted with methylene chloride or ethyl acetate, as desired. The organic layer is separated, dried and reduced under vacuum to residue. The residue was then recrystallized from ethyl acetate:hexane to result in N—CBZ 3-phenylisoserine ethyl ester.

This intermediate was next protected by the hydrogenatable benzyl-type protecting group in several ways. For example, one route to the desired hydrogenatable benzyl-type protected side chain is as follows:

Reaction III

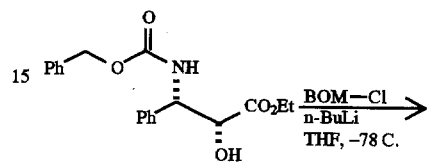

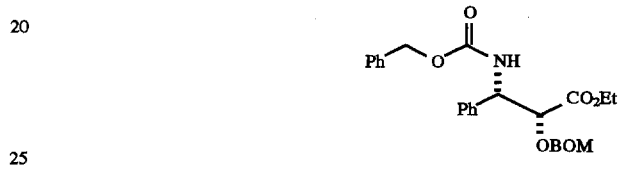

Reaction III

Here, the hydrogenable benzyl-type protecting group is benzyloxymethyl (BOM). To prepare this compound, the N—CBZ 3-phenylisoserine ethyl ester is dissolved in anhydrous THF under a nitrogen atmosphere and cooled to a reduced temperature such as −40° C. or −78° C., for example, in a dry ice/acetone bath followed by the dropwise addition of an alkyllithium agent such as n-butyl lithium, although it is desirable that the alkyllithium agent be a straight chain alkyl. In any event, the reaction is best done at a temperature no greater than 0° C. The resulting mixture is stirred for about ten minutes. Benzyloxymethyl chloride (BOM-Cl) is then added dropwise over an interval of about five minutes and the mixture stirred for approximately two to five hours at the reduced temperature. Thereafter, the solution is warmed to 0° C. and quenched with water to eliminate excess n-butyl lithium. The resulting mixture is reduced under vacuum to residue, and this residue is thereafter taken up in ethyl acetate and washed with water and brine to remove unwanted salts. The organic layer may then be dried and reduced under vacuum and the residue recrystallized from ethyl acetate:hexane or chromatographed with ethyl acetate:hexane to give the N—CBZ C2'-BOM 3-phenylisoserine ethyl ester.

Another route to production of N—CBZ C2'-OBOM 3-phenylisoserine ethyl ester is accomplished by dissolving the compound N—CBZ (2R,3S)-3-phenylisoserine ethyl ester in anhydrous methylene chloride. Thereafter, a tertiary amine base such as diisopropylethylamine is added along with BOM-Cl and the mix is refluxed for twenty-four hours. While this reaction route will produce N—CBZ 2'-BOM-3-phenylisoserine ethyl ester, the reaction proceeds much more slowly than the route discussed above. However, it may be preferred because of higher yield. Here, the compound is not purified, but rather is carried on to subsequent processing steps in crude form.

In either instance, the resulting N—CBZ C2'-OBOM (2R,3S)-3-phenylisoserine ethyl ester, either in the purified form of the first route or in the crude form from the second route, may simply be converted to the corresponding acid by the reaction:

Reaction IV

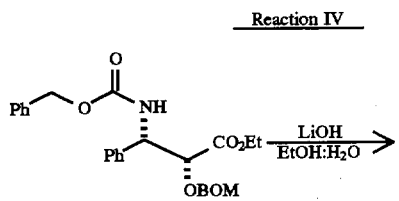

Reaction IV

Here, the protected ethyl ester is dissolved in ethanol/water (ratio 8:1). Lithium hydroxide (or other suitable alkali hydroxide) is added to the solution and the resulting mixture stirred for approximately three hours in order to saponify the compound. The mixture is then acidified (1N hydrochloric acid) and extracted with ethyl acetate. The resulting organic layer is separated, dried and reduced under vacuum. The residue acid is then isolated for use without further purification. This produces the desired N—CBZ C2'-OBOM (2R,3S)-3-phenylisoserine.

Where the N—CBZ C2'-OBOM 3-phenylisoserine ethyl ester is carried forward in the crude form and is converted into N—CBZ C2'-OBOM (2R,3S)-3-phenylisoserine, it is necessary for further purification of the end product. This purification is accomplished by dissolving the product in toluene followed by the dropwise addition of one equivalent of dicyclohexylamine and the resulting solution is stirred for one-half hour. This mixture is then concentrated in vacuo, and the resulting residue is recrystallized from ethyl acetate:hexane to give the dicyclohexylamine salt of the N—CBZ C2'-OBOM (2R,3S)-3-phenylisoserine. The purified N—CBZ C2'-OBOM (2R,3S)-3-phenylisoserine may then be liberated by dissolving this dicyclohexylamine salt in methylene chloride or another halogenated solvent followed by washing the methylene chloride with several portions of 1N HCl. The organic layer is then washed with several portions of water to remove dicyclohexylamine hydrochloride. Next, it is washed with one portion of saturated brine and reduced in vacuo to give the desired acid.

Benzyl itself is another example of a hydrogenatable benzyl-type protecting group that may be used instead of BOM. N—CBZ 2'-benzyl 3-phenylisoserine ethyl ester was produced as above with the substitution of benzyl bromide for BOM-Cl according to the reaction:

Reaction V

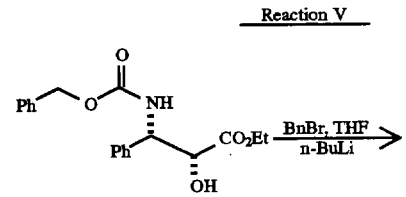

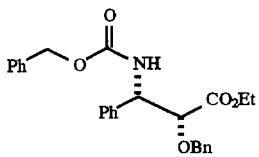

Reaction V

Here, the CBZ protected (2R,3S)-3-phenylisoserine ethyl ester is dissolved in anhydrous THF under a nitrogen atmosphere and cooled to a reduced temperature such as −40° C. or −78° C. for example in a dry ice/acetone bath followed by the dropwise addition of an alkyllithium agent such as n-butyl lithium, although it is desirable that the alkyllithium agent be a straight chain alkyl. The resulting mixture is stirred for about ten minutes. Benzyl bromide (BnBr) is then added dropwise over an interval of about five minutes and the mixture stirred for approximately two to five hours at the reduced temperature. Thereafter, the solution is warmed to 0° C. and quenched with water to destroy excess n-butyl lithium. The resulting mixture is reduced under vacuum to residue, and this residue is thereafter taken up in ethyl acetate and washed with water to remove any lithium bromide salt; it is then further washed with brine. The organic layer may the be dried and reduced under vacuum and the residue recrystallized from ethyl acetate:hexane or chromatographed with ethyl acetate:hexane to give N—CBZ 2'-benzyl 3-phenylisoserine ethyl ester.

Alternatively, the N—CBZ 2'-benzyl 3-phenylisoserine ethyl ester may be obtained according to the reaction:

Reaction VI

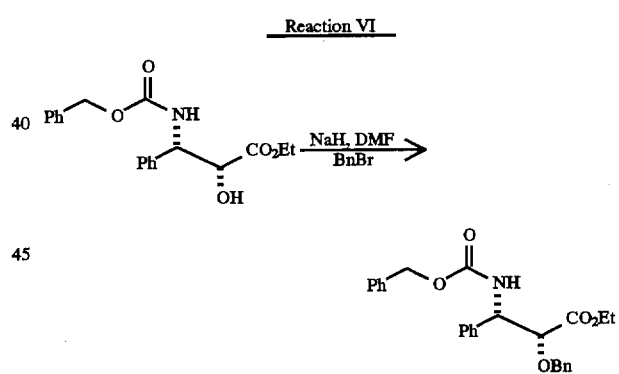

Reaction VI

Here, to a stirred solution of NaH in anhydrous DMF under nitrogen is added N—CBZ-3-phenylisoserine ethyl ester dissolved in DMF over five minutes. The mixture is then stirred at 0° C. for one half hour. Then benzyl bromide (1.1 equivalents) is added dropwise over five minutes and the reaction is stirred for two hours. The mixture is then quenched with water to destroy excess sodium hydride. Thereafter, either diethyl ether or methyl t-butyl ether is added. The organic layer is then washed with four portions of water to remove DMF and sodium bromide. Next, it is washed with brine and then dried and reduced under vacuum to produce N—CBZ C2'-benzyl 3-phenylisoserine ethyl ester may then be readily converted into N—CBZ C2'-benzyl 3-phenylisoserine by the process of Reaction IV above with the understanding that, in this case, benzyl is the C2' protecting group instead of benzyloxymethyl (BOM).

C. Esterification of the Protected Baccatin III with the Side Chain

Esterification of the C7, C10 di-CBZ 10-deacetylbaccatin III with the N—CBZ C2'-protected 3-phenylisoserine side chain (where the C2' hydroxyl is protected by any hydrogenatable benzyl-type group) is accomplished as follows. The preferred hydrogenatable benzyl group shown below is BOM (benzyloxymethyl).

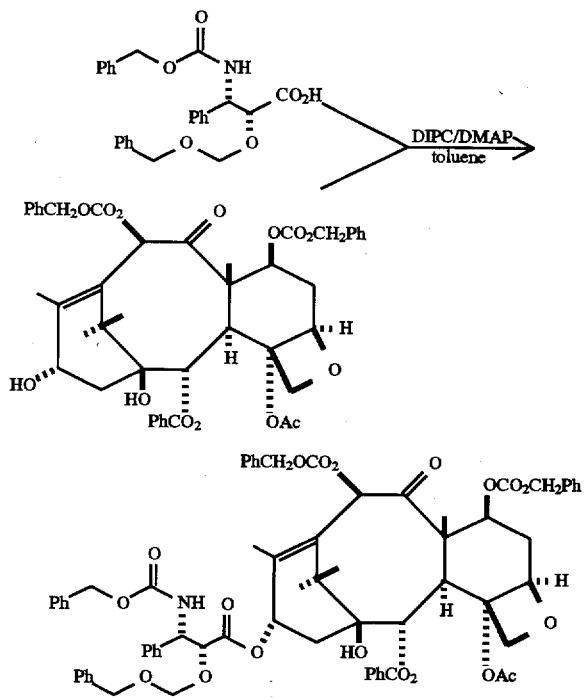

Reaction VII

Here, the C7, C10 di-CBZ 10-deacetylbaccatin III (1 equivalent) of Formula 1 and the acid side chain (6 equivalents) of Formula 2 are dissolved in toluene. To this mixture, 4-dimethylamino pyridine (DMAP) (one equivalent) and diisopropylcarbodiimide (6 equivalents) are added, and the resulting mixture heated at about 60° to 80° C. for one to five hours. It should also be noted, however, that other dialkylcarbodiimides may be substituted for the diisopropylcarbodiimide, with one example being dicyclohexylcarbodiimide.

The solution is then allowed to cool to room temperature, and next an equal volume of diethyl ether is added. The resulting solution is cooled to 0° C. and held at this temperature for twenty-four hours. This step crystallizes most of the urea impurity. After the twenty-four hour interval elapses, the solution is filtered and the residue rinsed with either ethyl ether or methyl t-butyl ether. The combined organics are then washed with hydrochloric acid (5%), water, and finally brine. The organic phase is separated, dried, and reduced under vacuum. The resulting residue is then dissolved in ethyl acetate:hexane and eluted over a silica gel plug. The eluent is then reduced under vacuum to result in the desired C3' NCBZ C2'-OBOM-C7, C10-di-CBZ 10-deacetyl baccatin III of the formula:

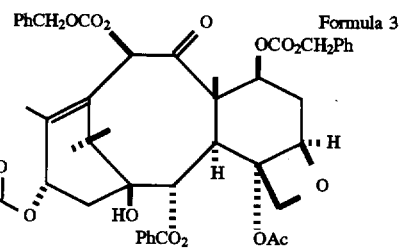

D. Deprotection and Treatment with Di-tert-Butyl dicarbonate and Deprotection to Form Docetaxel The following reaction removes the CBZ protecting groups at C7 and C10 and the C3' nitrogen side chain site. (Again for clarity, BOM is used here as an example of a C2' hydrogenatable benzyl-type protecting group):

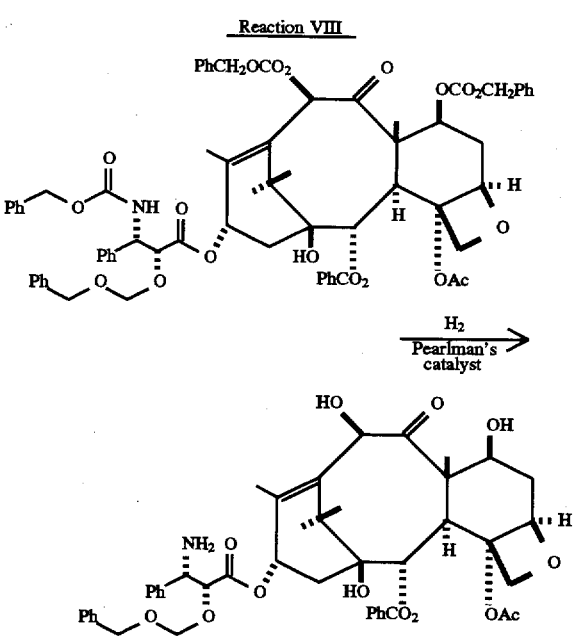

Reaction VIII

The coupled product of Formula 3 is dissolved in isopropanol/ethyl acetate to which Pearlman's catalyst is added. The resulting mixture is hydrogenated at 1 atmosphere of hydrogen for at least twenty-four hours. Thereafter, the mixture is filtered through diatomaceous earth and reduced under vacuum to residue to result in the amine shown which is used without further purification.

Next, the t-BOC group can be attached at the N-C3' side chain site according to the following reaction:

Reaction IX

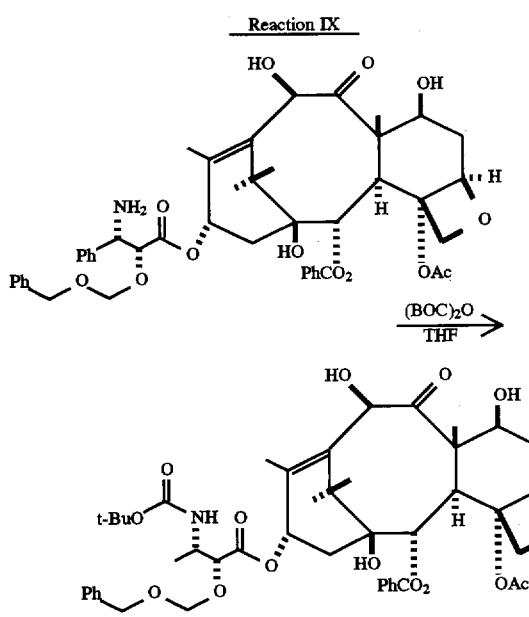

Reaction IX

Here, the amine is taken up in anhydrous THF and a tertiary amine base may be added to accelerate the reaction, followed by the addition of di-tert-butyldicarbonate. The mixture is stirred for twenty-four hours, and then reduced under vacuum and redissolved in ethyl acetate. The organic phase was then washed with water and brine. The resulting organic phase was then separated, dried, and reduced under vacuum to get crude C2'-OBOM docetaxel. It is necessary at this stage of processing to purify the crude C2'-OBOM docetaxel. This can be accomplished by column chromatography and/or recrystalization from ethyl/acetate:hexane. Preferably both column chromatography with ethyl/ acetate:hexane to produce an eluent that is reduced in vacuum to form a residue followed by recrystalization of the residue from ethyl acetate:hexane is employed to yield C2'-OBOM docetaxel in a substantially pure form.

The benzyloxymethyl protecting group is removed as follows:

Reaction X

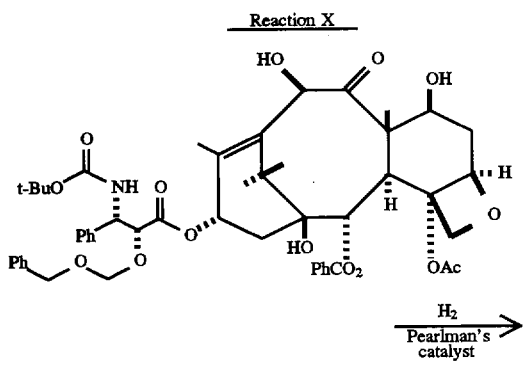

-continued
Reaction X

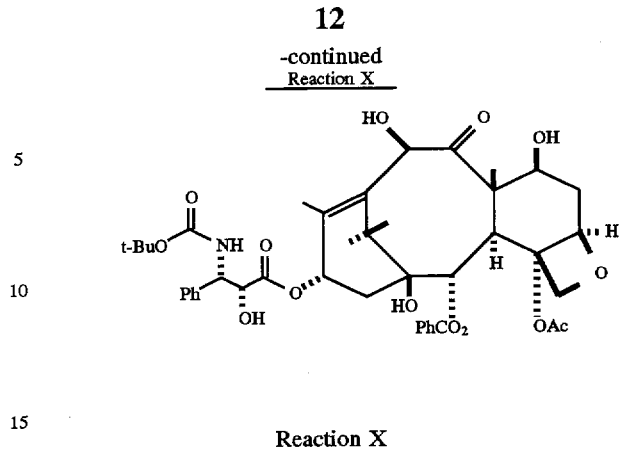

Reaction X

Here, the purified C2'-OBOM docetaxel is dissolved in isopropanol and Pearlmann's catalyst is added. The mixture is then hydrogenated at either 1 Atm of hydrogen or at 40 psi hydrogen for at least twenty-four hours. The mixture is then filtered through diatomaceous earth and reduced under vacuum to get crude docetaxel. Where the C2' side chain site has been protected with O-Bn, conversion to crude docetaxel may be accomplished according to the literature procedure (Kanazawa, A., Denis J. N. and Green, A. E. J. Org. Chem. 1994, 59, 1238).

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

We claim:

1. A method of producing docetaxel, comprising the steps of:

(a) esterifying C7, C10 di-CBZ 10-deacetyl baccatin III of the formula

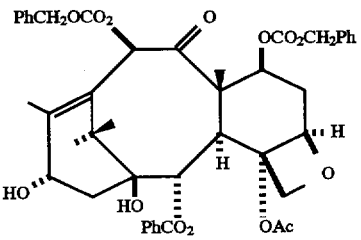

with an N—CBZ C2'-protected 3-phenyl isoserine side chain of the formula

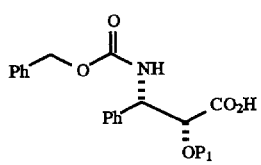

to form a first intermediate compound of the formula

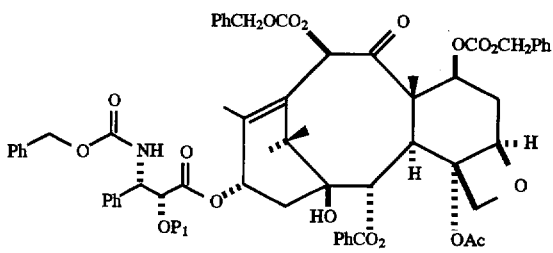

wherein $P_1$ is a hydrogenatable benzyl-type protecting group;

(b) substituting hydrogen for the C7, C10 carbobenzyloxy groups and substituting t-butoxycarbonyl for the carbobenzyloxy group at the C3' nitrogen site to form a second intermediate compound of the formula:

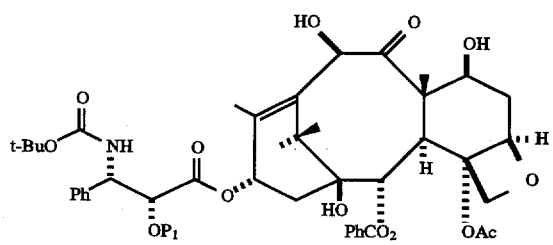

wherein $P_1$ is a hydrogenatable benzyl-type protecting group; and (c) deprotecting the second intermediate compound by substituting hydrogen for $P_1$ to produce docetaxel.

2. The method of producing docetaxel according to claim 1 wherein $P_1$ is selected from a group consisting of benzyloxymethyl and benzyl.

3. The method of producing docetaxel according to claim 1 wherein six equivalents of the N—CBZ C2'-protected 3-phenylisoserine side chain are used for each equivalent of C7, C10 di-CBZ 10-deacetyl baccatin III during the esterifying step.

4. The method of producing docetaxel according to claim 1 wherein the N—CBZ C2'-protected 3-phenylisoserine side chain and the C7, C10 di-CBZ 10-deacetyl baccatin III are dissolved in toluene to form a first solution during the esterifying step after which DMAP and a dialkylcarbodiimide is added to the first solution to produce a second solution containing the first intermediate compound.

5. The method of producing docetaxel according to claim 4 wherein the dialkylcarbodiimide is in equal proportion to the N—CBZ C2'-protected 3-phenylisoserine.

6. The method of producing docetaxel according to claim 4 wherein the dialkylcarbodiimide is selected from a group consisting of diisopropylcarbodiimide and dicyclohexylcarbodiimide.

7. The method of producing docetaxel according to claim 4 wherein the esterifying step is conducted at a first temperature of 60°–80° C. for a first interval.

8. The method of producing docetaxel according to claim 7 wherein diethyl ether is added to the second solution to produce a third solution that is then cooled to a reduced temperature sufficient to crystalline urea therefrom.

9. The method of producing docetaxel according to claim 1 wherein the esterifying step is conducted at a first temperature of 60°–80° C. from a first interval.

10. The method of producing docetaxel according to claim 1 wherein the first intermediate compound is dissolved in a solution and is column chromatographed to purify the first intermediate compound prior to replacing the C7, C10 and N-C3' carbobenzyloxy groups to form the second intermediate compound.

11. The method of producing docetaxel according to claim 1 wherein the step of substituting hydrogen for the C7, C10 carbobenzyloxy groups is conducted first to produce an amine, and t-butoxycarbonyl is subsequently substituted for the carbobenzyloxy group at the C3' nitrogen site to produce the second intermediate compound.

12. The method of producing docetaxel according to claim 11 wherein the step of substituting hydrogen for the C7, C10 carbobenzyloxy groups is accomplished by dissolving the first intermediate compound in isopropanol/ethyl acetate in a presence of Pearlman's catalyst to form a first mixture.

13. The method of producing docetaxel according to claim 12 wherein the first mixture is hydrogenated for at least twenty-four hours.

14. The method of producing docetaxel according to claim 11 wherein the step of substituting hydrogen for the carbobenzyloxy group at the C3' nitrogen site is accomplished by taking the amine up in tetrahydrofuran.

15. The method of producing docetaxel according to claim 14 wherein a tertiary amine base is added to the amine and tetrahydrofuran.

16. The method of producing docetaxel according to claim 14 wherein di-tert-butyldicarbonate is added to the amine and tetrahydrofuran to form a second mixture.

17. The method of producing docetaxel according to claim 16 wherein the second mixture is stirred for about twenty-four hours and reduced in vacuum, redissolved in ethyl acetate, and washed with water and brine to produce an organic phase which is then separated and chromatographed with ethyl acetate:hexane to produce an eluent containing the second intermediate compound in purified form.

18. The method of producing docetaxel according to claim 17 wherein the eluent is reduced in vacuum to a residue which is then recrystallized to produce the second intermediate compound in purified form.

19. The method of producing docetaxel according to claim 1 wherein the step of deprotecting the second intermediate compound is accomplished by dissolving the compound in isopropanol in the presence of Pearlman's catalyst to form a second mixture.

20. The method of producing docetaxel according to claim 19 wherein the second mixture is hydrogenated for at least twenty-four hours.

21. A method of producing docetaxel, comprising the steps of:

(a) esterifying C7, C10 di-CBZ 10-deacetyl baccatin III of the formula:

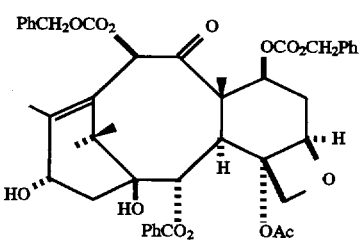

with an excess of N—CBZ C2'-protected 3-phenylisoserine side chain of the formula:

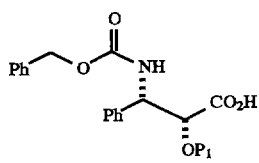

in solution with toluene and a dialkylcarbodiimide to produce a first intermediate compound of the formula:
  wherein $P_1$ is a hydrogenatable benzyl-type protecting group;
(b) substituting hydrogen for the C7, C10 and the C3' nitrogen carbobenzyloxy groups in the first intermediate compound by dissolving the first intermediate compound in isopropanol/ethyl acetate in a presence of Pearlman's catalyst to form a first mixture that is then hydrogenated to produce an amine;

(c) acylating at the C3' nitrogen site with t-BOC by taking the amine up in tetrahydrofuran and a tertiary amine base, followed by the addition of di-tert-butyldicarbonate to form C2'-$OP_1$ docetaxel; and
(d) deprotecting the C2'-$OP_1$ docetaxel by substituting hydrogen for $P_1$ to produce docetaxel.

22. The method of producing docetaxel according to claim 21 wherein $P_1$ is selected from a group consisting of benzyl and benzyloxymethyl.

23. The method of producing docetaxel according to claim 21 wherein $P_1$ is benzyloxymethyl and the deprotecting step is accomplished by dissolving the C2'-$OP_1$ docetaxel in isopropanol in a presence of Pearlman's catalyst to form a mixture that is then hydrogenated.

24. The method of producing docetaxel according to claim 21 wherein the excess of N—CBZ C2'-protected 3-phenylisoserine is at least six equivalents.

* * * * *

UNITED STATES PATENT AND TRADEMARK OFFICE
Certificate

Patent No. 5,688,977                                                                    Patented: November 18, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Nicholas J. Sisti, Pepperell, MA; Charles S. Swindell, Merion, PA; Madhavi C. Chander, Boulder, CO.

Signed and Sealed this Thirtieth Day of March 2004.

MARIANNE C. SEIDEL
*Supervisory Patent Examiner*
Art Unit 1600